United States Patent [19]

Edwards et al.

[11] Patent Number: 5,363,861
[45] Date of Patent: Nov. 15, 1994

[54] ELECTRODE TIP ASSEMBLY WITH VARIABLE RESISTANCE TO BENDING

[75] Inventors: Stuart D. Edwards, Los Altos; Russell B. Thompson, San Leandro, both of Calif.

[73] Assignee: EP Technologies, Inc., Sunnyvale, Calif.

[21] Appl. No.: 789,260

[22] Filed: Nov. 8, 1991

[51] Int. Cl.⁵ .................. A61B 5/00; A61M 25/00; A61M 37/00
[52] U.S. Cl. .................. 128/772; 128/639; 604/95; 604/264; 606/129; 607/115; 607/122
[58] Field of Search .................. 600/11; 128/399–402, 128/783, 786, 639, 642, 772, 639, 642; 604/95, 264; 606/129; 607/1, 115–118, 122

[56] References Cited

U.S. PATENT DOCUMENTS

| | | | |
|---|---|---|---|
| 3,612,058 | 10/1971 | Ackerman | 604/95 |
| 4,763,647 | 8/1988 | Gambale | 128/772 |
| 4,920,980 | 5/1990 | Jackowski | 128/642 |
| 5,231,989 | 8/1993 | Middleman | 604/95 |
| 5,238,005 | 8/1993 | Imran | 604/95 |

FOREIGN PATENT DOCUMENTS

| | | | |
|---|---|---|---|
| 8002231 | 10/1980 | WIPO | 607/122 |
| 9111213 | 8/1991 | WIPO | 604/95 |

Primary Examiner—Randall L. Green
Assistant Examiner—P. Zuttarelli
Attorney, Agent, or Firm—Ryan, Kees & Hohenfeldt

[57] ABSTRACT

An electrode tip assembly for a catheter is bendable under the control of the user. One portion of the assembly is more resistant to bending than the remaining portions. The variable stiffness directs and concentrates the applied bending forces in the particular region where maximum bending is desired.

7 Claims, 8 Drawing Sheets

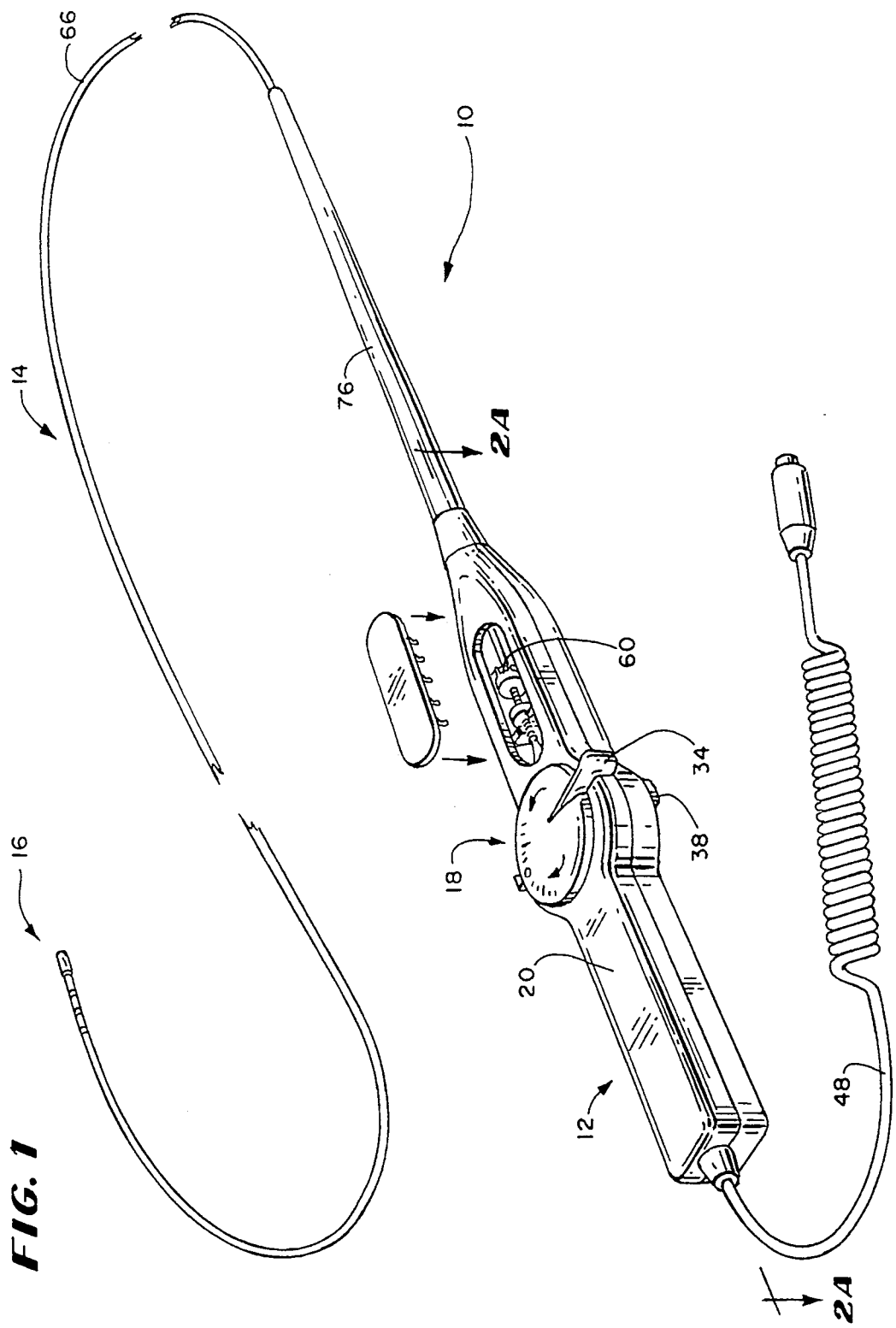

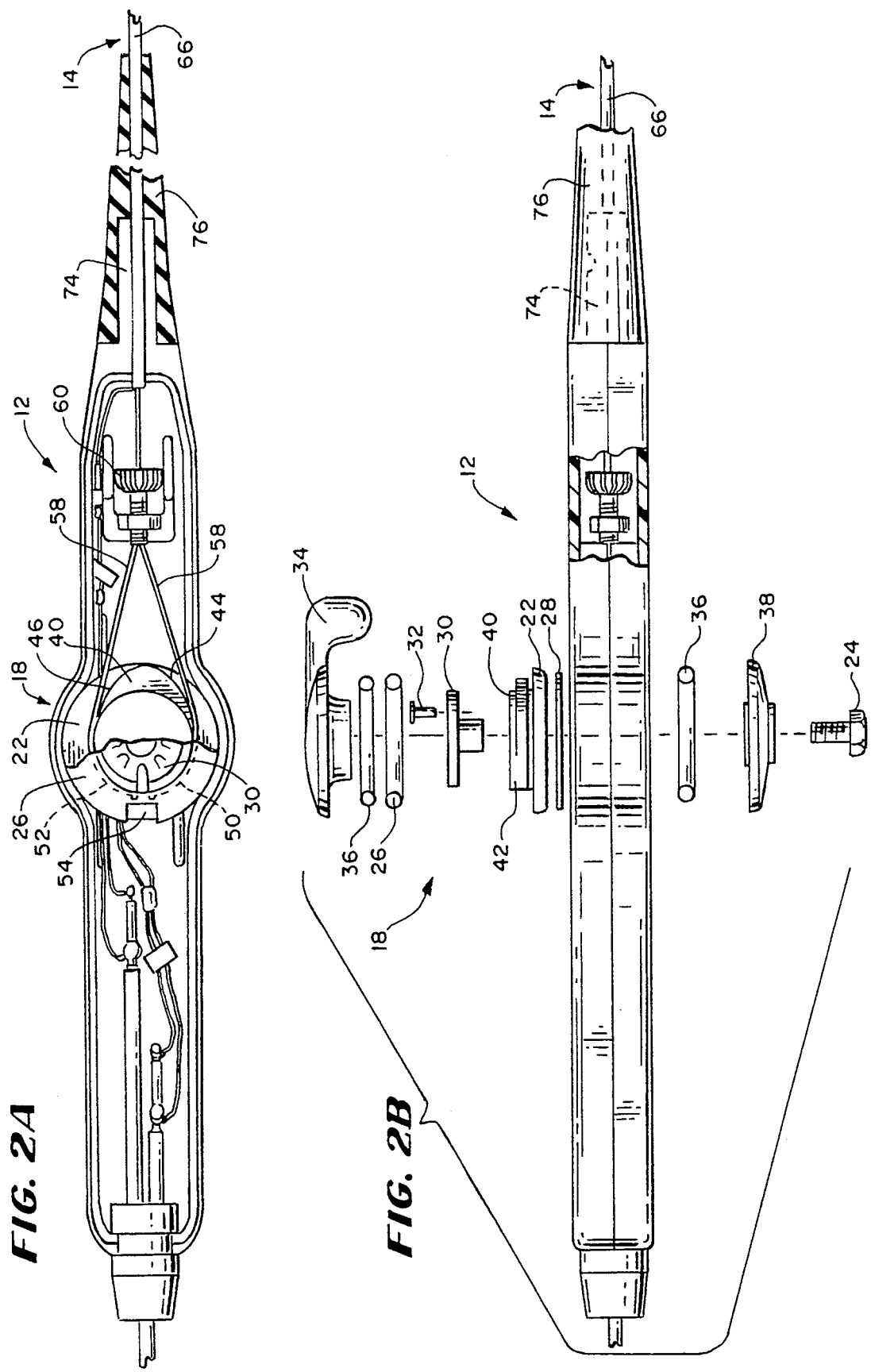

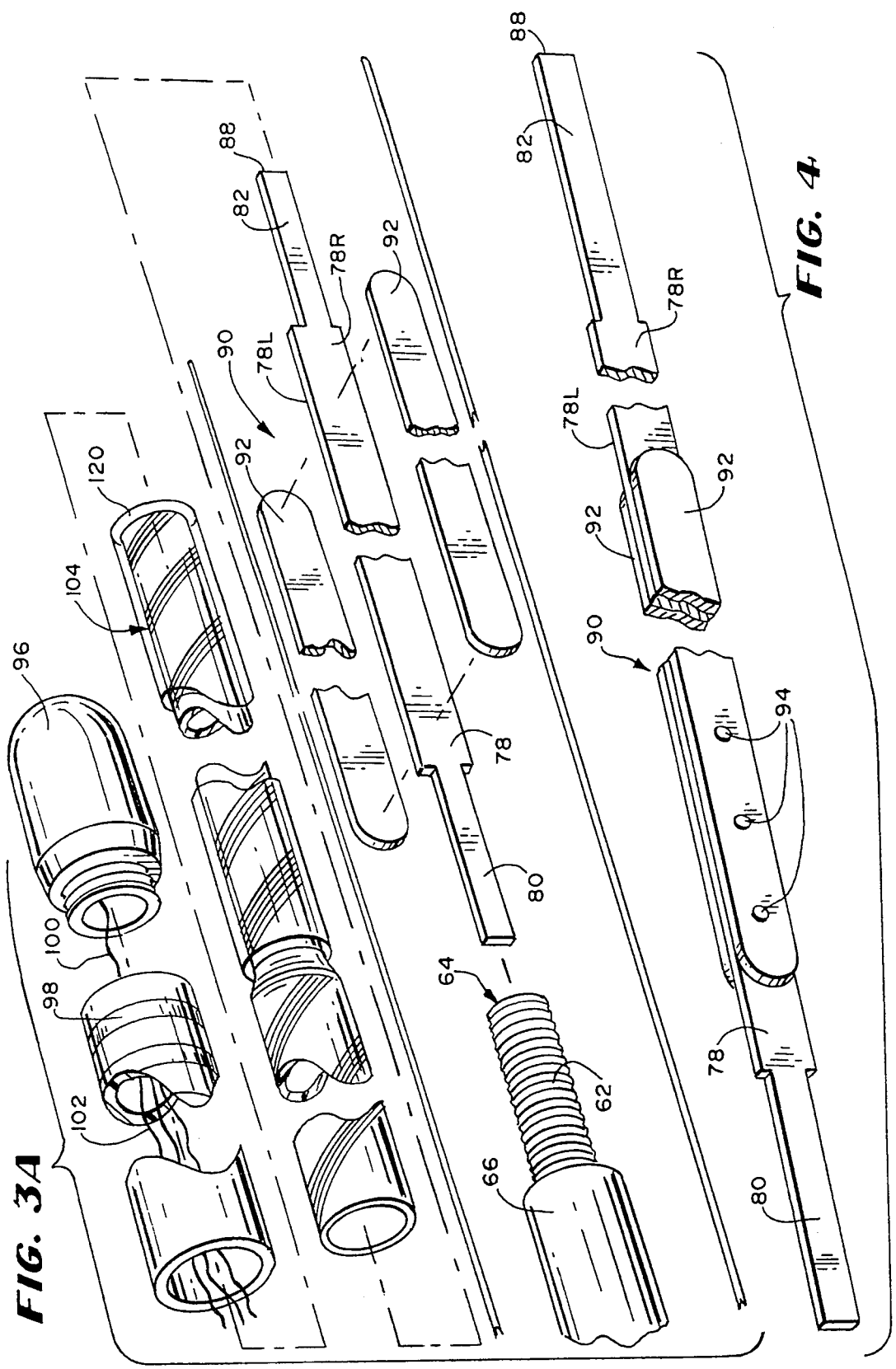

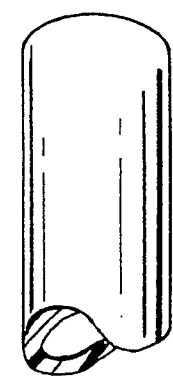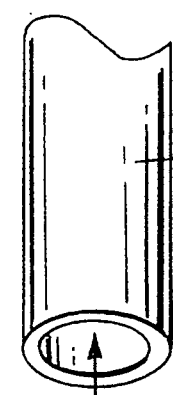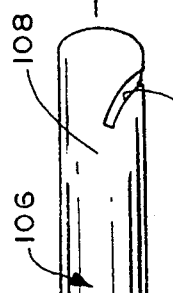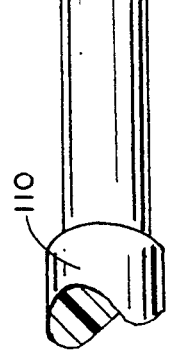
FIG. 5A
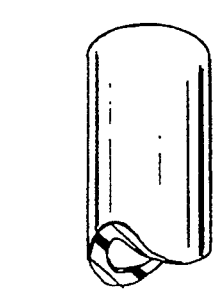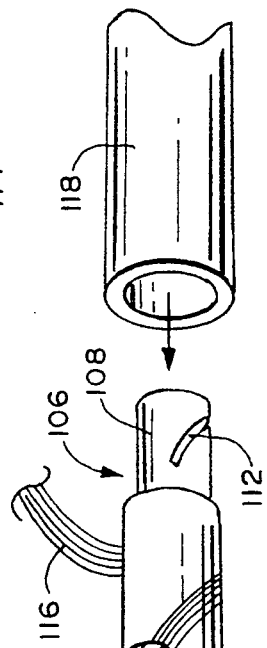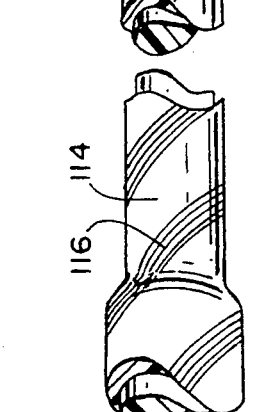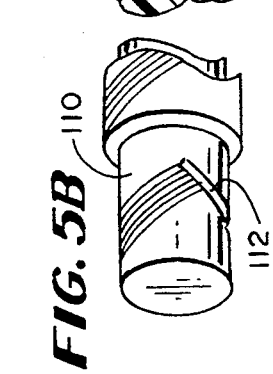
FIG. 5B
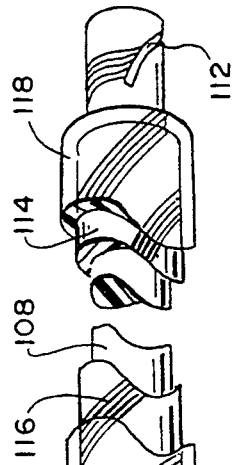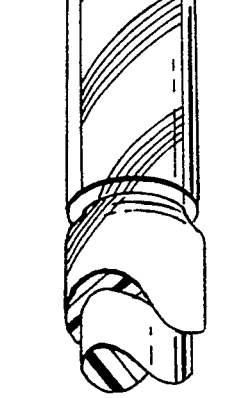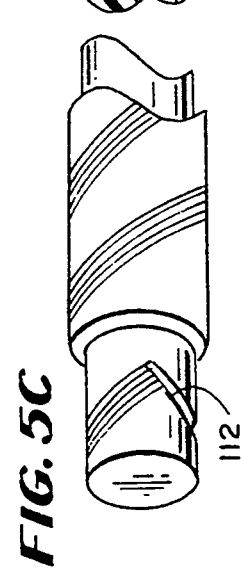
FIG. 5C
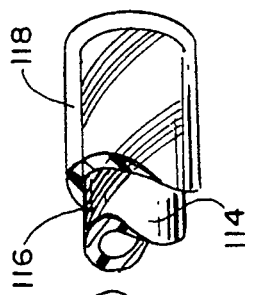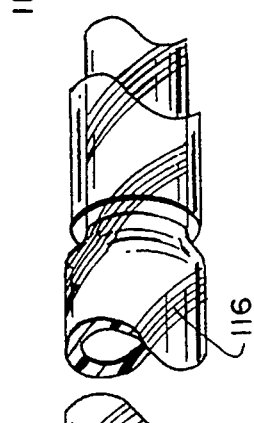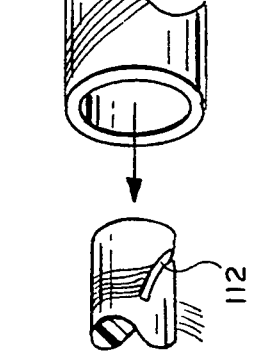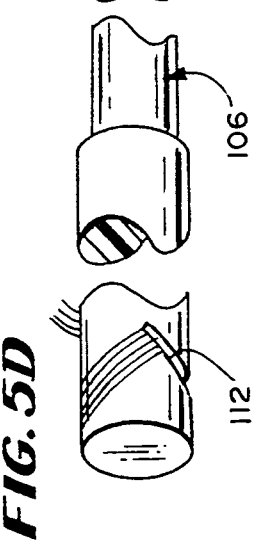
FIG. 5D

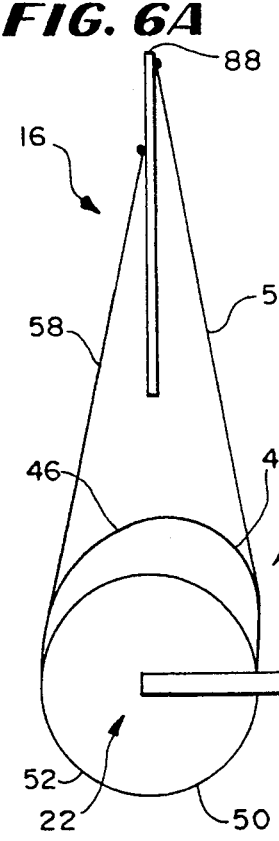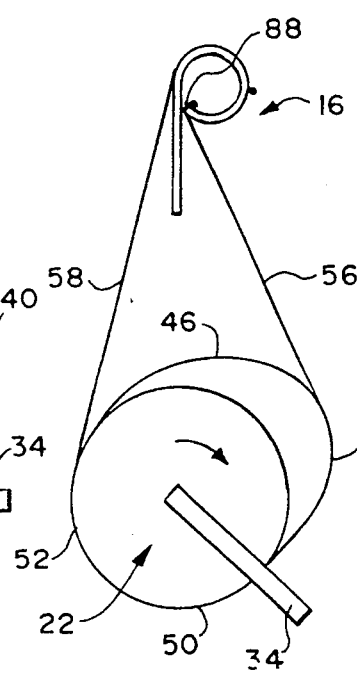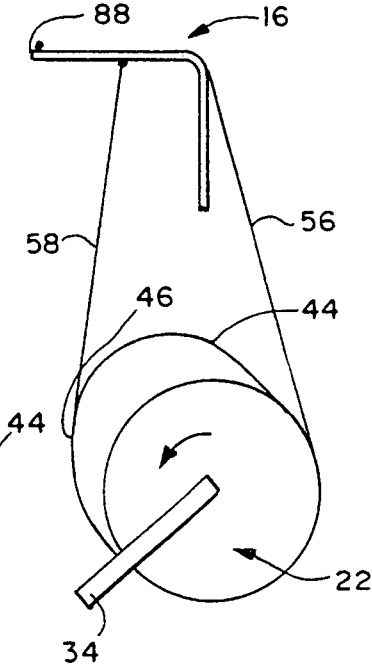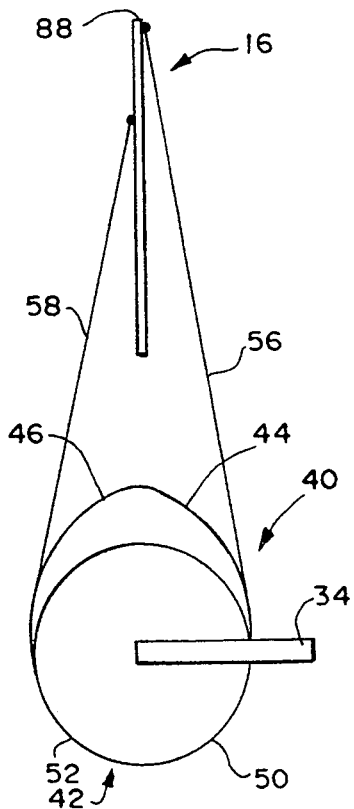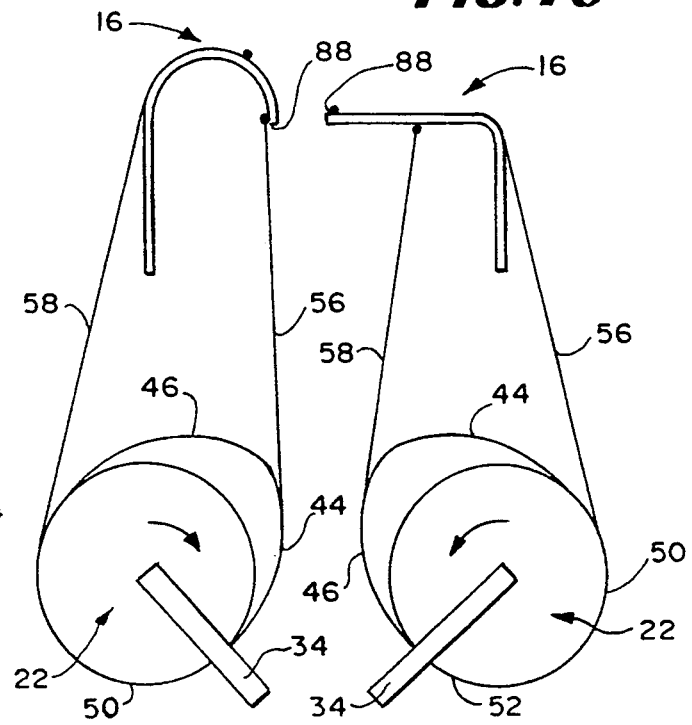

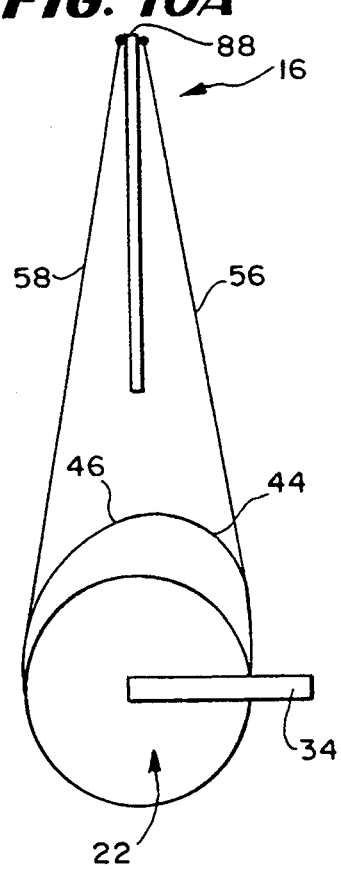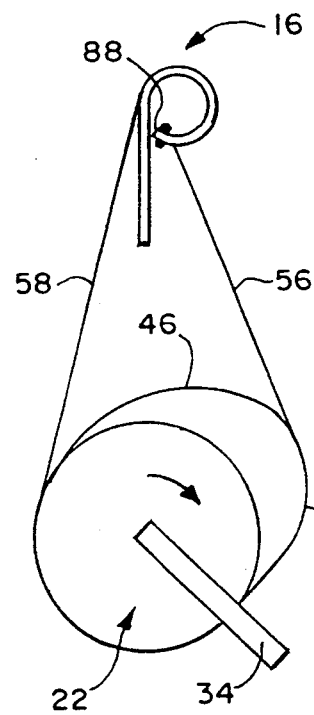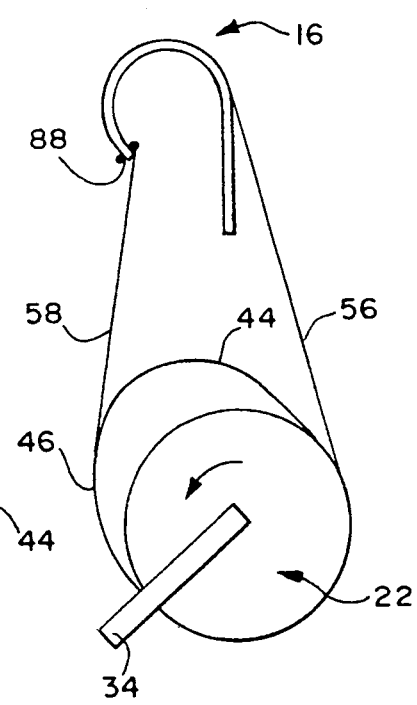

ELECTRODE TIP ASSEMBLY WITH VARIABLE RESISTANCE TO BENDING

FIELD OF THE INVENTION

The invention generally relates to catheters. In a more specific sense, the invention relates to catheters that can be steered and manipulated within interior regions of the body from a location outside the body.

BACKGROUND OF THE INVENTION

Physicians make widespread use of catheters today in medical procedures to gain access into interior regions of the body. It is important that the physician can control carefully and precisely the movement of the catheter within the body.

The need for careful and precise control over the catheter is especially critical during procedures that ablate tissue within the heart. These procedures, called electrophysiological therapy, are becoming more widespread for treating cardiac rhythm disturbances.

During these procedures, a physician steers a catheter through a main vein or artery (which is typically the femoral arterial) into the interior region of the heart that is to be treated. The physician then further manipulates a steering mechanism to place the electrode carried on the tip of the catheter into direct contact with the tissue that is to be ablated. The physician directs radio frequency energy into the electrode tip to ablate the tissue and form a lesion.

Cardiac ablation especially requires the ability to precisely bend and shape the tip end of the catheter to position the ablation electrode.

SUMMARY OF THE INVENTION

The invention provides an electrode tip assembly for a catheter that is bendable under the control of the user. One portion of the assembly is more resistant to bending than the remaining portions. The variable stiffness directs and concentrates the applied bending forces in the particular region where maximum bending is desired.

In one embodiment, the electrode tip assembly includes an interior body bendable in response to external forces. The body has opposite end portions. One end portion attaches to the guide tube of a catheter. The other end portion is adjacent the tip electrode.

The stiffening mechanism varies the stiffness of the body between its end portions so that the end portion attached to the catheter is more resistant to bending than the other end portion adjacent the tip electrode. In this way, bending forces are concentrated at the tip of the assembly, where the electrode is located.

In a preferred embodiment, the stiffening mechanism includes two springs that sandwich a portion of the bendable body between them.

BRIEF DESCRIPTION OF THE DRAWINGS

FIG. 1 is a perspective view of a catheter that embodies the features of the invention;

FIG. 2A is a side section view of the catheter taken generally along line 2A—2A in FIG. 1;

FIG. 2B is an exploded view of FIG. 2A;

FIG. 3A is an exploded view of the electrode tip assembly of the catheter;

FIG. 4 is a perspective view of the stiffening assembly for the support wire of the catheter;

FIGS. 5A to D show the assembly of reinforcing tube that surrounds the support wire of the catheter;

FIGS. 6A to C show the steering mechanism for Curve Option 1 of the catheter;

FIGS. 7A to C show the steering mechanism for Curve Option 2 of the catheter;

FIGS. 10A to C show the steering mechanism for Curve Option 5 of the catheter.

DESCRIPTION OF THE PREFERRED EMBODIMENTS

Figure 3B:
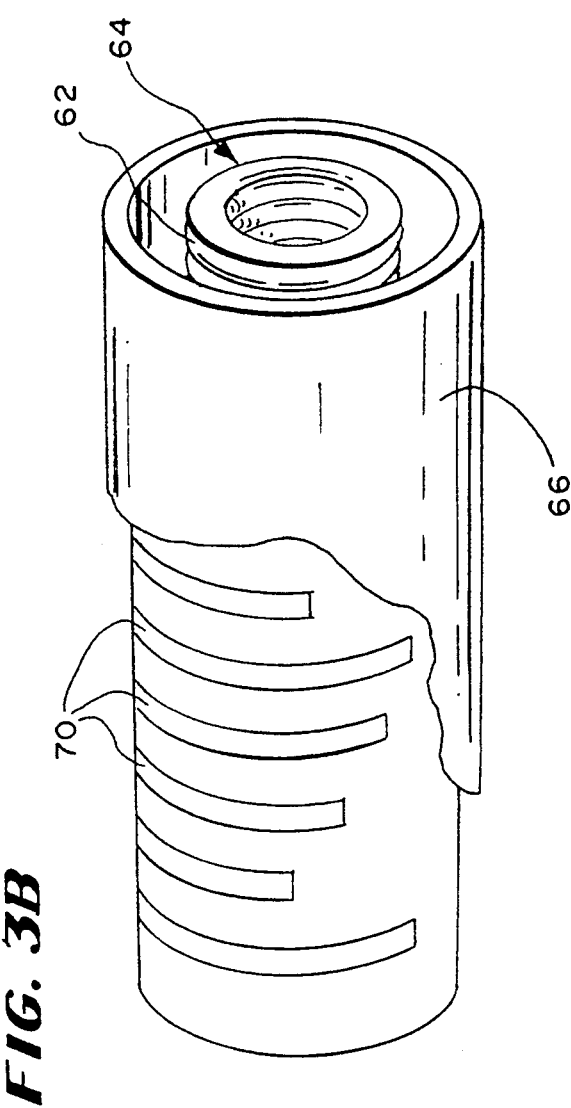
FIG. 3B is a view of an alternative guide tube shaft for the catheter.

FIG. 1 shows the assembly of a steerable catheter 10 that embodies the features of the invention. As there shown, the catheter 10 includes three main parts or assemblies: the handle assembly 12, the guide tube assembly 14, and the electrode tip assembly 16.

The catheter 10 can be used in many different environments. This specification will describe the catheter 10 as used to provide electrophysiologic therapy in the interior regions of the heart.

When used for this purpose, a physician grips the handle assembly 12 to steer the guide tube assembly 14 through a main vein or artery (which is typically the femoral arterial) into the interior region of the heart that is to be treated. The physician then further manipulates a steering mechanism 18 on the handle assembly 12 (which will be described later) to place the electrode tip assembly 16 in contact with the tissue that is to be ablated. The physician directs radio frequency energy into the electrode tip assembly 16 to ablate the tissue contacting the electrode tip assembly 16.

As FIGS. 2A and 2B best show, the handle assembly 12 includes a housing 20 that encloses the steering mechanism 18. The steering mechanism 18 includes a rotating cam wheel 22 carried on a screw 24 within the housing 20. The cam wheel 22 is seated for rotation between a top washer 26 and a bottom washer 28. A lock nut 30 and a pin 32 couple an external steering lever to the top of the cam wheel 22. The steering lever 34 seats against an O-ring 36.

Movement of the steering lever 34 by the user rotates the cam wheel 22 about the screw 24 within the housing 20. Clockwise movement of the steering level rotates the cam wheel 22 to the right. Counterclockwise movement of the steering wheel rotates the cam wheel 22 to the left. Contact between the steering lever 34 and the side of the housing 20 physically limits the range of left and right rotation of the cam wheel 22 within the housing 20.

The steering mechanism 18 also includes an external locking lever 38 that an adhesive couples to the head of the screw 24. The locking lever 38 seats against another O-ring 36.

Movement of the locking lever 38 rotates the screw 24. Clockwise rotation of the locking lever 38 tightens the screw 24 to increase the seating force between the cam wheel 22 and the bottom washer 28. When moved fully clockwise into contact against the housing 20, the locking lever 38 imposes a seating force that prevents rotation of the cam wheel 22 by the steering lever 34. Counterclockwise movement of the locking lever 34 loosens the screw 24 to decrease the seating force and free the cam wheel 22 for rotation.

The cam wheel 22 includes a forward cam face 40 and a rear cam face 42. The forward cam face 40 is oriented toward the front of the housing 20, where the guide tube assembly 14 attaches. The forward cam face includes a right side surface 44 and a left side surface 46.

The rear cam face 42 is oriented toward the back of the housing 20, where a coaxial cable 48 attaches. The rear cam face includes right and left side surfaces 50 and 52.

The cam wheel 22 also carries a wire fastener 54 between the right and left side surfaces 50 and 52 of the rear cam face 42. The wire fastener 54 holds the proximal ends of right and left catheter steering wires 56 and 58, which are soldered to the interior of the fastener 54.

The steering wires 56 and 58 extend from the opposite ends of the fastener 54 and along the associated left and right side surfaces 44/46 and 50/52 of the front and rear cam faces 40 and 42. The steering wires exit the front of the housing 20 through the interior bore of a tension screw assembly 60.

As will be described in greater detail later, the distal ends of the steering wires 56 and 58 are attached to the electrode tip assembly 16. They extend from the wire fastener 54 through the guide tube assembly 14 to the electrode tip assembly 16.

As also will be described in greater detail, the wire fastener 54 in association with the cam faces 40 and 42 translate rotation of the cam wheel 22 into lateral pulling movement of the steering wires 56 and 58 attached to the electrode tip assembly 16.

By rotating the cam wheel 22 to the left (by moving the steering lever 34 counterclockwise), the left steering wire 58 bears against the left front and rear cam surfaces 46 and 52. The cam surfaces 46 and 52 tension the left steering wire 58 to impose a discrete, constant pulling force that causes the electrode tip assembly 16 to bend to the left.

Also, by rotating the cam wheel 22 to the right (by moving the steering lever 34 clockwise), the right steering wire 56 bears against the right front and rear cam surfaces 44 and 56. The cam surfaces 44 and 56 tension the right steering wire 56 to impose a discrete, constant pulling force that causes the electrode tip assembly 16 to bend to the right.

Rotation of the tension screw assembly 60 additionally varies the amount of slack (i.e., tension) in the steering wires 56 and 58 between the wire fastener 54 and the distal ends of the steering wires 56 and 58. This controls the responsiveness of the electrode tip assembly 16 to rotation of the cam wheel 22.

The component parts of the handle assembly 12 can be constructed of various materials, depending upon the durability needed and the sterilization process used.

For example, when EtO sterilization is used, the housing 20 and bottom washer 28 can be made of a polycarbonate material. In this arrangement, the cam wheel 22, steering lever 34, and locking lever 38 can be made of a delrin material. These plastic materials are durable and EtO sterilizable. In this assembly, the lock nut 30, pin 32, and screw 24 are preferably made of a metallic material like brass or stainless steel.

As FIG. 3A shows, the guide tube assembly 14 includes a flexible shaft 62 attached to the handle assembly 12. The flexible shaft 62 encloses an interior bore 64. The steering wires 56 and 58 pass through the interior bore 64.

The shaft 62 may constructed in various ways. In the embodiment shown in FIG. 3, the shaft 62 comprises a length of stainless steel coiled into a flexible spring enclosing the interior bore 64. A braided sheath 66 of plastic material encloses the coil.

Alternatively (as FIG. 3B shows), the shaft 62 comprises a slotted, stainless steel tube enclosing the interior bore 64. An array of slots 70 subtends the tube along its length. The slots 70 subtend less than one circumference of the shaft 62 at an angle of between 270 to 300 degrees. The slots 70 are also radially offset one from the other by about 30 to 120 degrees.

The slotted shaft 62 shown in FIG. 3B provides strength and flexibility along the length of the guide tube assembly 14. The slotted shaft 62 also transmits twisting motions (torque) from the handle assembly 12 to the electrode tip assembly 16 more directly than the coiled shaft 62 shown in FIG. 3. Further details of the slotted shaft 62 are disclosed in pending Lundquist U.S. patent application Ser. No. 07/657,106 filed Feb. 15, 1991 and entitled "Torquable Catheter 10 and Method."

Like the coiled shaft 62 in FIG. 3A, a sheath 66 encloses the slotted shaft. The sheath 66 is made from a plastic material, such as polyolefin.

The handle assembly 12 includes a tubular stem 74 though which the proximal end of the guide tube assembly 14 extends for attachment to the tension screw assembly 60. Adhesive attaches the proximal end of the coil to the tension screw assembly 60.

The guide tube assembly 14 can be made in various lengths. In the illustrated, the guide tube assembly 14 is about 100 cm in length.

As FIGS. 1 and 2A/B show, a sleeve 76 couples the guide tube assembly 14 to the handle assembly 12. Adhesive secures one end of the sleeve 76 to the handle stem 74. The sleeve 76 includes an interior bore that progressively tapers from the handle stem 74 into a tight interference fit about the sheath 66 of the guide tube assembly 14. The exterior of the sleeve 76 also tapers, extending about 4 to 5 inches beyond the front of the handle housing 20.

The sleeve 76 is made of a material having a high coefficient of friction, like Krayton G2703. The sleeve 76 provides a gripping surface to help the user manipulate the catheter 10. When used in association with the slotted tube, the sleeve 76 also significantly enhances the transmission of torque from the handle assembly 12 to the electrode tip assembly 16 through the guide tube assembly 14.

The electrode tip assembly 16 includes a bendable main support wire 78 having left and right faces 78L and 78R. In the illustrated embodiment, the main support wire 78 is made of stainless steel flat wire stock in an elongated shape about 0.035 inch wide and about 0.005 inch thick. The main support wire 78 is about 3 inches in total length.

The opposite ends of the main support wire 78 are cut away to form stepped shoulders 80 and 82. In the illustrated embodiment, the shoulders 80 and 82 are about 0.024 inch wide and aligned along the centerline of the main support wire 78. Each shoulder 80 and 82 is about 0.12 inch in length.

As FIG. 3A shows, one stepped shoulder 80 fits within the distal end of the flexible guide tube shaft 62 to append the electrode tip assembly 16 to the guide tube assembly 14. When properly oriented, the left and right faces 78L and 78R of the main support port wire 78 lie in a plane that is generally parallel to the axis about which the cam wheel 22 rotates. Stated differently, when the user holds the handle assembly 12 in a horizontal plane, the left and right faces 78L and 78R of the main support wire 78 lie in a vertical plane.

As FIG. 3A shows, the distal end of the left steering wire 58 is soldered to the left face 78L of the main support wire 78. When pulled by left rotation of the cam wheel 22, the left steering wire 58 bends the main support wire 78 to the left.

Also, the distal end of the right steering wire 56 is soldered to the right face 78R of the main support wire 78. When pulled by right rotation of the cam wheel 22, the right steering wire 56 bends the main support wire 78 to the right.

In the illustrated embodiment, the stiffness of the main support wire 78 is not uniform, but varies along its length. Its stiffest point is near its proximal end region, where it joins the guide tube shaft 62. Its stiffness is least at the tip end 88 of the shoulder 82. By varying the stiffness of the main support wire 78 between its proximal end and its distal tip end 88, the base of the electrode tip assembly 16 (where it joins the guide tube assembly 14) resists bending and buckling. The bending forces generated by the steering wires 56 and 58 are directed toward the distal tip end 88 of the main support wire 78. The variable stiffness of the main support wire 78 concentrates the bending forces at the distal tip end 88 of the electrode tip assembly 16.

There are various ways to varying the stiffness of the main support wire 78 along its length. One way (not shown) is to vary the thickness of the main support wire 78 as it is manufactured, so that it is thickest (i.e., most stiff) near the shoulder 80 that, in use, is fitted within the guide tube shaft 62.

In the illustrated and preferred embodiment (see FIG. 4), a stiffening spring assembly 90 stiffens the center support near the distal end of the guide tube shaft 62. The stiffening spring assembly 90 includes two leaf springs 92 that sandwich the main support wire 78 between them. Each leaf spring 92 is made of stainless steel flat wire stock in an elongated shape that is about 0.039 inch wide and about 0.0029 inch thick.

The stiffening spring assembly 90 can sized and configured to provide the degrees of stiffness and variance wanted. In the illustrated embodiment, the stiffening spring assembly 90 stiffens the main support wire 78 beginning about 0.030 to 0.050 inch from the inner edge of the attachment shoulder 80 and extending from there about 1.5 inches.

In the illustrated embodiment, spot welds 94 secure the leaf springs 92 to the main support wire 78. The three spot welds 94 shown are clustered near the proximal end of the stiffening spring assembly 90. There, they are evenly spaced, with the most distal spot weld 94 being about 0.10 inch from the proximal end of the stiffening spring assembly 90.

In the illustrated embodiment, the distal end of the electrode tip assembly 16 carries an ablation tip electrode 96 and three ring electrodes 98. Interior conducting wires 100 are connected to the tip electrode 96 and the three ring electrodes 98. The conducting wires 100 extend along the main support wire 78, through the interior bore of the guide tube shaft 62, and into the handle housing 20 to join the coaxial cable 48 that extends from the rear of the housing 20.

The coaxial cable 48 ends with plugs 102. The plugs 102 connect with appropriate conventional catheter control equipment (not shown). The conducting wires 100 transfer electrical current from the ring electrodes 98 indicative of electrical activity within the heart. The conducting wires 100 also transfer radio frequency energy to the tip electrode 96 to carry out ablation procedures within the heart.

There are various ways of securing the attachment between the electrode tip assembly 16 and the guide tube assembly 14. The illustrated embodiment employs a reinforcing sleeve assembly 104 for this purpose.

As shown in the FIGS. 5A to D, the reinforcing sleeve assembly 104 is made in association with a specially designed sleeve mandrel 106. In the illustrated embodiment, the sleeve mandrel 106 is made from stainless steel and is about 7 inches in total length. As FIG. 5A shows, the mandrel 106 has a first cylindrical body portion 108 and second cylindrical body portion 110 having an enlarged diameter. In the illustrated embodiment, the first body portion 108 is about 0.032 inch in diameter and is about 5 inches long. The second body portion 110 has an enlarged diameter of about .043 inch and is about 2 inches long. The first body portion 108 and the second body portion 110 each includes an inwardly sloping notch 112.

In making the reinforcing sleeve assembly 104 (see FIG. 5A), a sleeve mandrel 106 receives a first heat shrink tube 114 that, in the illustrated embodiment, is about 4.5 inches long. A portion of the first tube 114 is pulled over the second body portion 110 of the mandrel 106. Heat is applied using an oven or heat gun to shrink the tube in place upon the sleeve mandrel 106.

Next (see FIG. 5B), a reinforcing fabric 116 is wrapped in tension over the first tube 114 while still on the mandrel 106. The fabric 116 is wrapped as a single spiral about the first tube 114 to obtain a desired, closely spaced pitch. In the illustrated embodiment the fabric 116 is wrapped to a pitch of about 18 to 20 wraps per inch. The notches 112 on the sleeve mandrel 106 hold the fabric 116 in tension during this step of the manufacturing process.

The mandrel 106 now receives a second heat shrink tube 118 over the fabric-wrapped first tube 114 (see FIGS. 5B and 5C). The second tube 118 is shorter than the first tube 114, and is not pulled over the second body portion 110 of the sleeve mandrel 106. In the illustrated embodiment, the second tube 118 is about 4.0 inches long.

Heat is again applied using an oven or heat gun to shrink the second tube 118 in place over the fabric-wrapped first tube 114. When shrunk in place, the second tube 118 captures and encases the wrapped fabric 116 and underlying first tube 114 (as FIG. 5C shows).

Next (see FIG. 5D), the fabric 116 extending from the second tube 118 to the notches 112 is cut away. The reinforcing sleeve assembly 104 is removed from mandrel 106.

The reinforcing sleeve assembly 104 is inserted over the main support wire 78 appended to the distal end of the guide shaft 62 (see FIG. 3A) so that the enlarged diameter portion of the reinforcing sleeve assembly 104 slips over the distal end of the guide shaft 62. At this time, the left and right steering wires 56 and 58 and stiffening spring assembly 90 are attached to the main support wire 78. The conducting wires 100 also extend along the main support wire 78 and into the bore of the guide shaft 62.

Heat is again applied using an oven or heat gun to finally shrink the second tube 118 in place over distal end of the guide shaft 62 and over the main support wire 78 and its associated parts. When finally shrunk in place, the reinforcing sleeve assembly 104 tightly encases the main support wire 78.

The wrapped fabric 116 becomes an integrated part of the reinforcing sleeve assembly 104. The reinforcing sleeve assembly 104 is flexible enough to accommodate the bending movement desired for the electrode tip assembly 16. Still, due to the wrapped fabric 116, the reinforcing sleeve assembly 10 provides added strength and resistance against wear and tear during repeated bending operations.

The reinforcing sleeve assembly 104 also holds the steering wires 56 and 58 and conducting wires 100 in close intimate contact against the main support wire 78. The intimate contact prevents kinking and chafing of the steering wires 56 and 58 and conducting wires 100 during bending operations.

The materials used to make the reinforcing sleeve assembly 104 can vary. In the illustrated embodiment, the shrink tubes 114 and 118 are made from medical grade TFE Teflon material having a 2 to 1 shrink ratio. The material used has a wall thickness (after heat shrinkage) of about 0.003 to 0.0045 inch. In the illustrated embodiment, the fabric 116 is a Kevlar 49 Yarn (which is available from DuPont). This material has a tensile strength of about 400,000 lbs/in$^2$ and a modulus of about 18,000,000 lbs/in$^2$.

An outer tube 120 covers the reinforcing sleeve assembly 104. The tip electrode 96 and ring electrodes 98 are attached to the conducting wires 100 and joined to the outer tube 120 by conventional methods to complete the electrode tip assembly 16.

In the illustrated embodiment, the curvature assumed upon bending the electrode tip assembly 16 to the left is different that the curvature assumed upon bending the electrode tip assembly 16 to the right. The electrode tip assembly 16 assumes one curvature when bent to the left and a different curvature when bent to the right. These different left and right curvatures provide the physician with flexibility in steering the tip electrode 96 into position. These differing curvatures will be called asymmetric curves.

The drawings show five representative asymmetric curve options that embody the features of the invention. The invention achieves the different curve options by varying two relationships.

The first relationship is that between the cam radius on the left side surfaces 46 and 52 of the forward cam and rear cam faces 40 and 42, and the cam radius on the right side surfaces 44 and 50 of the forward and rear cam faces 40 and 42. According to the invention, the cam radii differ, forming various asymmetric cam arrangements.

The second relationship is that between the point of attachment of the left steering wire 58 on the left face 78L of the main support wire 78 and the point of attachment of the right steering wire 56 on the right face 78R of the main support wire 78. According to the invention, the point of attachment can be varied, forming both symmetrical and asymmetric steering wire attachment sites.

Combinations of asymmetric cam arrangements and symmetrical and asymmetric steering wire attachments create differing asymmetric curve options. The five curve options shown are intended to illustrate the ideas of forming asymmetric curves by varying the two relationships, but they do not encompass all the possible curve options that can be made.

Asymmetric Curve Option 1

As FIGS. 6A to C show, the catheter 10 includes an asymmetric forward cam face 40 on the cam wheel 22 and a symmetrical rear cam face 42. In addition, the electrode tip assembly 16 includes asymmetric attachments of the left and right steering wires 56 and 58 to the left and right faces 78L and 78R of the main support wire 78.

More particularly, the right side surface 44 of the forward cam face 40 is formed with a radius of 0.3125 inch, while the left side surface 46 of the forward cam face 40 is formed with a radius of 0.4062 inch. The right and left side surfaces 50 and 52 of the rear cam face 42 each has a radius of 0.313".

The right steering wire 56 is attached at the distal tip 88 of the main support wire 78, while the left steering wire 58 is attached about 1.5 inches from the distal tip 88 of the main support wire 78.

When the steering lever 34 is rotated clockwise, the foregoing relationships bend the main support wire 78 about 270 degrees to the right to form a looping "pigtail" curve. When the steering lever 34 is rotated counterclockwise, the foregoing relationships bend the main support wire 78 about 90 degrees to the left to form an elbow curve.

Assymmetric Curve Option 2

As FIGS. 7A to C show, the catheter 10 includes symmetrical forward and rear cam faces 40 and 42 on the cam wheel 22 in combination an asymmetric attachment of the left and right steering wires 56 and 58 to the main support wire 78 to achieve the asymmetric left and right curves in Option 2.

More particularly, the right side surface 44 and the left side surface 46 of the forward cam face 40 are both formed with a radius of 0.4062 inch. The right side surface 50 and the left side surface 52 of the rear cam face 42 are both formed with a radius of 0.313".

The right steering wire 56 is attached at the distal tip 88 of the main support wire 78, while the left steering wire 58 is attached about 1.5 inches from the distal tip of the main support wire 78.

When the steering lever 34 is rotated clockwise, the foregoing relationships bend the main support wire 78 about 135 degrees to the right to form an open, arching curve. When the steering lever 34 is rotated counterclockwise, the foregoing relationships bend the main support wire 78 about 90 degrees to the left to form an elbow curve (just as in Curve Option 1).

Assymmetric Curve Option 3

Figure 8A:
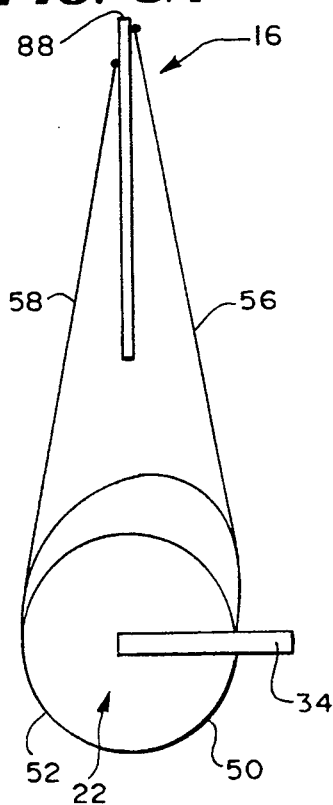
FIGS. 8A to C show the steering mechanism for Curve Option 3 of the catheter.
Figure 8B:
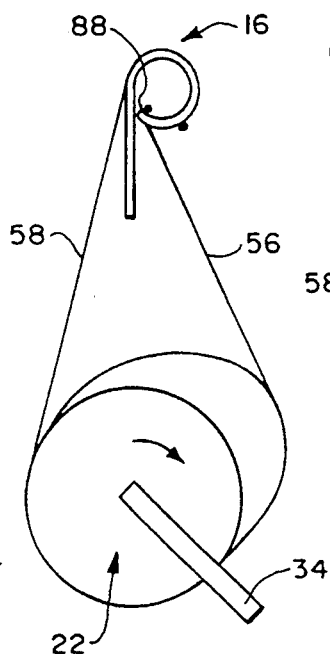
Figure 8C:
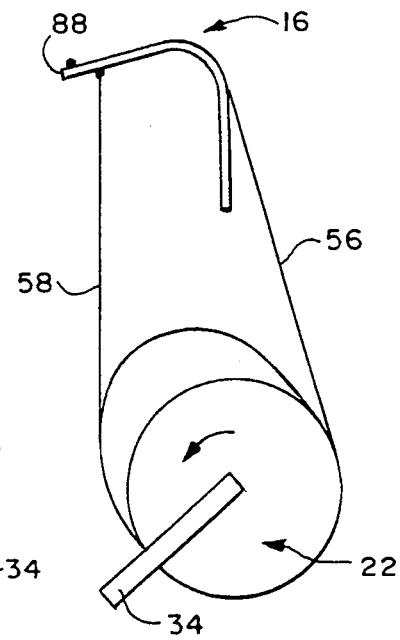

As FIGS. 8A to C show, the catheter 10 includes an asymmetric forward cam face 40 on the cam wheel 22 and a symmetrical rear cam face 42. In addition, the electrode tip assembly 16 includes symmetrical attachments of the left and right steering wires 56 and 58 to the left and right faces 78L and 78R of the main support wire 78.

More particularly, the right side surface 44 of the forward cam face 40 is formed with a radius of 0.3125 inch, while the left side surface 46 of the forward cam face 40 is formed with a radius of 0.4062 inch. The right and left side surfaces 50 and 52 of the rear cam face 42 each has a radius of 0.313".

The right and left steering wires 56 and 58 are attached at the distal tip 88 of the main support wire 78.

When the steering lever 34 is rotated clockwise, the foregoing relationships bend the main support wire 78 about 270 degrees to the right to form a looping "pigtail" curve (as in Curve Option 1, where the same cam and steering wire relationships exist on the right side). When the steering lever 34 is rotated counterclockwise, the foregoing relationships bend the main support wire 78 about 80 degrees to the left to form a partial arch.

Assymmetric Curve Option 4

Figure 9A:
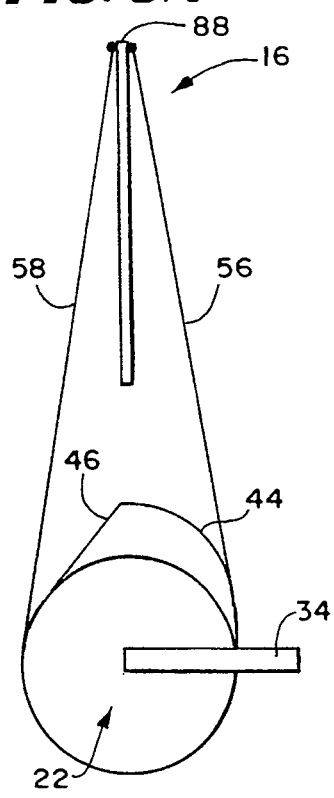
FIGS. 9A to C show the steering mechanism for Curve Option 4 of the catheter.
Figures 9B, 9C:
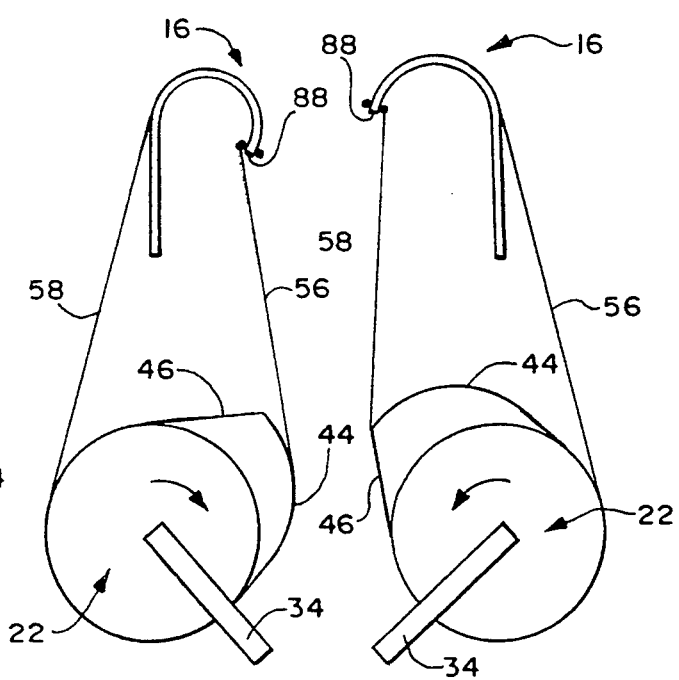

As FIGS. 9A to C show, both forward and rear cam faces 40 and 42 on the cam wheel 22 are asymmetric. The electrode tip assembly 16 includes a symmetrical attachment of the left and right steering wires 56 and 58 to the main support wire 78.

More particularly, the right side surface 44 of the forward cam face 40 is formed with a radius of 0.3125 inch. The left side surface 52 of the forward cam face 40 is formed as a straight (i.e., linear) line. The linear line extends along a tangent from an interior hub 68 of the cam wheel 22 to intersect the curved (i.e., nonlinear) right side surface 44.

The left side surface 52 of the rear cam face 42 extends arcuately from the tangent along the circumference of the interior hub 68. In contrast, the right side surface 50 is asymmetrically formed with a radius of 0.313".

The right steering wire 56 and the left steering wire 52 are both attached at the distal tip 88 of the main support wire 78.

When the steering lever 34 is rotated clockwise, the foregoing relationships bend the main support wire 78 in an open arch about 135 degrees. When the steering lever 34 is rotated counterclockwise, the foregoing relationships bend the main support spring in a tighter arch about 135 degrees to the left to form a "shepard's crook" curve.

Asymmetric Curve Option 5

As FIGS. 10A to C show, the catheter 10 includes an asymmetric forward cam face 40 and a symmetrical rear cam face 42. The electrode tip assembly 16 includes symmetrical attachments of the left and right steering wires 56 and 58 to the main support wire 78.

More particularly, the right side surface 50 of the forward cam face 40 is formed with a radius of 0.3125 inch, while the left side surface 46 of the forward cam face 40 is formed with a radius of 0.4062 inch. The left and right side surfaces 50 and 52 of the rear cam face 42 are each formed with a radius of 0.313".

The right steering wire 56 and the left steering wire 58 are both attached at the distal tip 88 of the main support wire 78.

When the steering lever 34 is rotated clockwise, the foregoing relationships bend the main support spring about 270 degrees to the right to form the looping "pigtail" curve (as in Curve Options 1 and 3). When the steering lever 34 is rotated counterclockwise, the foregoing relationships bend the main support spring about 135 degrees to the left to form a "shepard's crook" curve (like the right curve in Curve Option 4).

The following table summarizes the relationships that were varied to achieve Curve Options 1 to 5.

TABLE 1

| Curve Option | Asymmetric Curve Options 1 to 5 | | | |
| --- | --- | --- | --- | --- |
| | Left Wire | Left Cam* | Right Wire | Right Cam* |
| 1 | 1.5" | .4062" | Tip | .3125" |
| 2 | 1.5" | .4062" | Tip | .4062" |
| 3 | 0.75" | .4062" | Tip | .3125" |
| 4 | Tip | Linear | Tip | .4062" |
| 5 | Tip | .4062" | Tip | .3125" |

= *Note:
These columns refer to the left and right cam surfaces on the front cam face. In Curve Options 1, 2, 3 and 5, the left and right cam surfaces of the rear cam face are symmetrical, having a radius of .313". In Curve Option 4, the left and right cam surfaces of the rear cam are asymmetric, with the right cam surface formed with a radius of .3125 inch and the left cam face being linear (not curved).

Various features of the invention are set forth in the following claims.

We claim:

1. An electrode tip assembly for a catheter including
a support wire having a stiffness and being bendable in response to external forces, the support wire having proximal and distal opposite end portions, the proximal end portion being carried by the catheter body,
a stiffening spring contiguous to the wire and being attached to a side thereof for varying the stiffness of the support wire between its proximal and distal opposite end portions so that one of said end portions is more resistant to bending than the other of said end portions in response to an applied bending force, and
at least one steering wire attached to a side of said support wire for applying a bending force thereto.

2. A tip assembly according to claim 1
wherein the stiffening spring stiffens the proximal end portion and the steering wire is attached to the distal end portion.

3. An electrode tip assembly according to claim 1 wherein a tip electrode is carried on the distal end of said assembly.

4. An electrode assembly according to claim 3 wherein the stiffening spring is attached closer to the proximal end than to the distal end thereby making the proximal end more resistant to bending than the distal end.

5. A catheter including
a guide tube having a distal end,
an electrode tip assembly positioned on said distal end including
a support wire having a stiffness and being bendable in response to external forces, the support wire having a proximal end attached to the guide tube distal end and a distal end that extends beyond the guide tube distal end, and
a stiffening spring contiguous to and being attached to said support wire between its proximal and distal ends for varying the stiffness of the support wire between its proximal and distal end portions so that one end portion is more resistant to bending than the other end portion in response to an applied bending force.

6. A catheter according to claim 5
wherein first and second spring members sandwich the support wire between them.

7. A catheter according to claim 5
wherein the stiffening spring is attached closer to the proximal end of the support wire than to the distal end of the support wire, thereby making the proximal end of the support wire more resistant to bending than the distal end.

* * * * *